United States Patent [19]

Hoeck

[11] Patent Number: 4,544,529
[45] Date of Patent: Oct. 1, 1985

[54] BOTTLE STERILIZER

[76] Inventor: Horst Hoeck, Am Adamshäuschen 8, 5100 Aachen, Fed. Rep. of Germany

[21] Appl. No.: 449,749

[22] Filed: Dec. 14, 1982

[30] Foreign Application Priority Data

Dec. 16, 1981 [DE] Fed. Rep. of Germany ....... 3149754

[51] Int. Cl.⁴ .............................................. A61L 2/00
[52] U.S. Cl. .................................... 422/303; 211/74; 211/76; 422/297; 422/298; 422/300; 422/302; 422/310
[58] Field of Search ............... 422/297, 298, 300, 302, 422/303, 310; 211/74, 76

[56] References Cited

U.S. PATENT DOCUMENTS

| | | | |
|---|---|---|---|
| 1,983,390 | 12/1934 | Mueller | 422/303 |
| 2,029,844 | 2/1936 | Tyler | 422/303 |
| 2,141,516 | 12/1938 | Clements | 422/303 |
| 2,471,303 | 5/1949 | Brewster | 422/303 |
| 2,475,407 | 7/1949 | Sell | 422/303 X |
| 2,501,193 | 3/1950 | Schulte | 422/303 |

FOREIGN PATENT DOCUMENTS 2035278  6/1980  United Kingdom ................ 422/303

*Primary Examiner*—Barry S. Richman
*Assistant Examiner*—William R. Johnson

*Attorney, Agent, or Firm*—Karl F. Ross; Herbert Dubno

[57] ABSTRACT

An electric egg cooker is converted to a baby bottle sterilizer by mounting an insert thereon formed with seats for the baby bottles and nipples. A hood, which can be fitted over this insert, has a height sufficient to accommodate the baby bottles. The insert comprises a synthetic resin plate formed unitarily with a downwardly extending ridge engageable over a rim of an upwardly open water receiving pan, an upwardly extending ridge along upstanding ribs with cut out portions oriented such that three angularly equispaced ribs at each of a multiplicity of locations so as to define recesses therein providing for a plurality of seats including bottle seats dimensioned to receive infant-feeding bottles and nipple seats dimensioned to receive nipples for said bottles, the plate being provided with respective openings within the seats for permitting steam formed in the pan to rise through the opening and contact bottles and nipples located on the seats; respective upwardly extending tubes aligned with the openings of the bottle seats having upwardly converging frustoconical bases covering the openings of the bottle seats whereby steam is delivered to the upper end of inverted bottles placed on the bottle seats, the bottle seats holding the bottles out of contact with the bases.

4 Claims, 3 Drawing Figures

BOTTLE STERILIZER

FIELD OF THE INVENTION

My present invention relates to a bottle sterilizer and, more particularly, to a sterilizer for infant-feeding bottles and nipples and especially to an attachment for an egg cooker which will permit the same to be used in the home sterilization of baby bottles.

BACKGROUND OF THE INVENTION

It has long been recognized that a sterilizaiton of an infant-feeding bottle and nipple, with or without a cap for securing the nipple to the bottle, is advantageous in protecting the infant against pathogenic microorganisms which might be present in the environment or in the milk or formula to be fed to the infant.

The term "sterilization" is used in the sense of inactivation or killing of microorganisms which might be detrimental to the health of the infant.

Naturally, sterilization has been practiced for considerable time on an industrial and medical level and even to various degrees in the home by boiling the bottles and nipples for example.

It is also known to sterilize articles with hot air, with or without circulation, at temperatures of at least 180° C., and to generate somewhat superheated steam at a superatmospheric pressure of, say, 1 atmosphere gauge and a temperature of 120° C. and to contact the articles with the steam.

Modern industrial practice also utilizes electromagnetic energy, for example, ultraviolet radiation, gamma radiation and beta radiation, for the sterilization of articles in large measure. All these techniques, however, are unsuited for household application and hence domestic sterilization has concentrated on simple boiling.

Note should also be taken of the fact that a somewhat more efficient approach is utilized in hospitals and clinics and in stations for the large scale preparation of infant-feeding packages, wherein the bottles and/or nipples can be sterilized in autoclaves with superheated steam or water at elevated temperatures.

Another domestic approach to sterilization is to soak the bottles and nipples for a long period of time in sterilizing solutions, e.g. solutions of chlorine, and thereafter rinse the bottles.

Problems are encountered with most of the methods hitherto used for home sterilization of baby bottles. For example, when a disinfectant agent is utilized, there is always the danger of residual contamination of the bottle or nipple with the disinfectant. Indeed, residues of the disinfectant may accumulate with time on the bottles or the nipples and ultimately may be transferred to the infant, thereby endangering his or her health.

The rinsing of the bottles and nipples in nonsterile water, as is necessary for removal of residues, likewise poses a danger of reintroduction of infectious material.

Boiling likewise can result in residues on the sterile bottles and nipples and frequently is not capable of removing pathogenic microorganisms.

OBJECTS OF THE INVENTION

It is the principal object of the present invention to provide an improved sterilizer for one or more infant feeding bottles and nipples.

Another object of the invention is to provide an attachment for an egg cooker, of a type frequently available in the home, to enable improved sterilization of infant feeding bottles and nipples.

Still another object of the invention is to provide an improved steam sterilization system for infant feeding bottles and nipples whereby the disadvantages of chemical sterilization systems are obviated.

SUMMARY OF THE INVENTION

The invention is based upon my discovery that a conventional egg cooker, frequently found in the home, can be readily transformed into a baby bottle and nipple sterilizer capable of contacting the articles to be sterilized with steam and thereby efficiently sterilizing them without contact with a liquid-borne agent and without the disadvantages of boiling the articles.

The household egg cooker with which the present invention is concerned and with which the present invention can be used, comprises a base provided with an electric heating element and with a cooking pan overlying this base and adapted to be covered in turn with a hood.

In this type of egg cooker an insert supporting the eggs is capable of holding them above the water in the pan and enclosing them in the hood so that they can be cooked to the desired degree by steam generated by the electric heating of the water in the pan.

The hood is formed with a venting opening through which excess steam can escape and the base can be provided with temperature monitoring or other circuit means for cutting off heating of the water at an appropriate point.

The existence of this unit in many homes allows a solution of the problem described according to the invention.

According to the invention, therefore, a bottle sterilization insert is used in place of the egg-holding insert of the unit and is provided with at least one seat or holder for at least one baby bottle and at least one seat or holder for at least one nipple, each being constructed so that both the bottle and the nipple have their mouths turned downwardly toward the pan and communicate via openings of the respective seats and holders with the space below this insert and above the water in the pan.

The hood of the conventional egg cooker can also be replaced by a hood adapted to fit on the insert which has a sufficient height to accommodate the longest infant-feeding bottles commonly marketed.

According to the invention, the bottle holder is formed with at least one tube reaching upwardly into the bottle and terminating just below the closed end of the inverted bottle for delivering the steam to the bottle at this latter end.

According to another feature of the invention, the insert can be provided with a plurality of such holders and an angularly equally spaced relationship of nipple holders between the bottle holders.

The steam feeders of the holder can be simple openings in a plate with which the holders can be aligned and the holders can be formed by ribs, e.g. in a star array so that each of the articles to be sterilized is supported on three angualry spaced ribs preferably molded integrally from a heat-resistant synthetic resin material to form the insert.

The hood can be formed also from heat-resistant synthetic resin material, preferably by deep drawing.

According to the invention, moreover, a second hood can be provided with which the sterilized articles can be covered.

The invention is based upon my discovery that, utilizing this system, infant feeding bottles and nipples can be treated with steam practically at 100° C. as it rises from the water-boiling pan and can effectively be sterilized when the steam is conducted into the articles and permitted to flow onto the articles within the hood.

Apparently the unique results are at least in part due to the fact that both internal and external surfaces are contacted by the steam and the steam condenses upon all of these surfaces with liberation of the latent heat of evaporation raising the temperature thereof.

What is even more surprising is that the comparatively small amount of water utilized in a conventional egg cooker of the type described is effective to sterilize the milk bottles and nipples and hence that the larger quantities of water hitherto used even for boiling the bottles are not necessary.

Naturally, when the automatic controller cuts off the apparatus, e.g. upon a temperature rise as the water boils out, sterilization will be complete.

BRIEF DESCRIPTION OF THE DRAWING

The above and other objects, features and advantages of the present invention will become more readily apparent from the following description, reference being made to the accompanying drawing in which:

FIG. 3 is a diagrammatic elevational view of the base of the sterilizer.

SPECIFIC DESCRIPTION

The apparatus of the invention utilizes the lower portion of an egg cooker, namely the base 1 which is provided with an electric heater (see FIG. 3) and is covered by a cooking pan 2 adapted to receive a small quantity of water.

Figure 1:
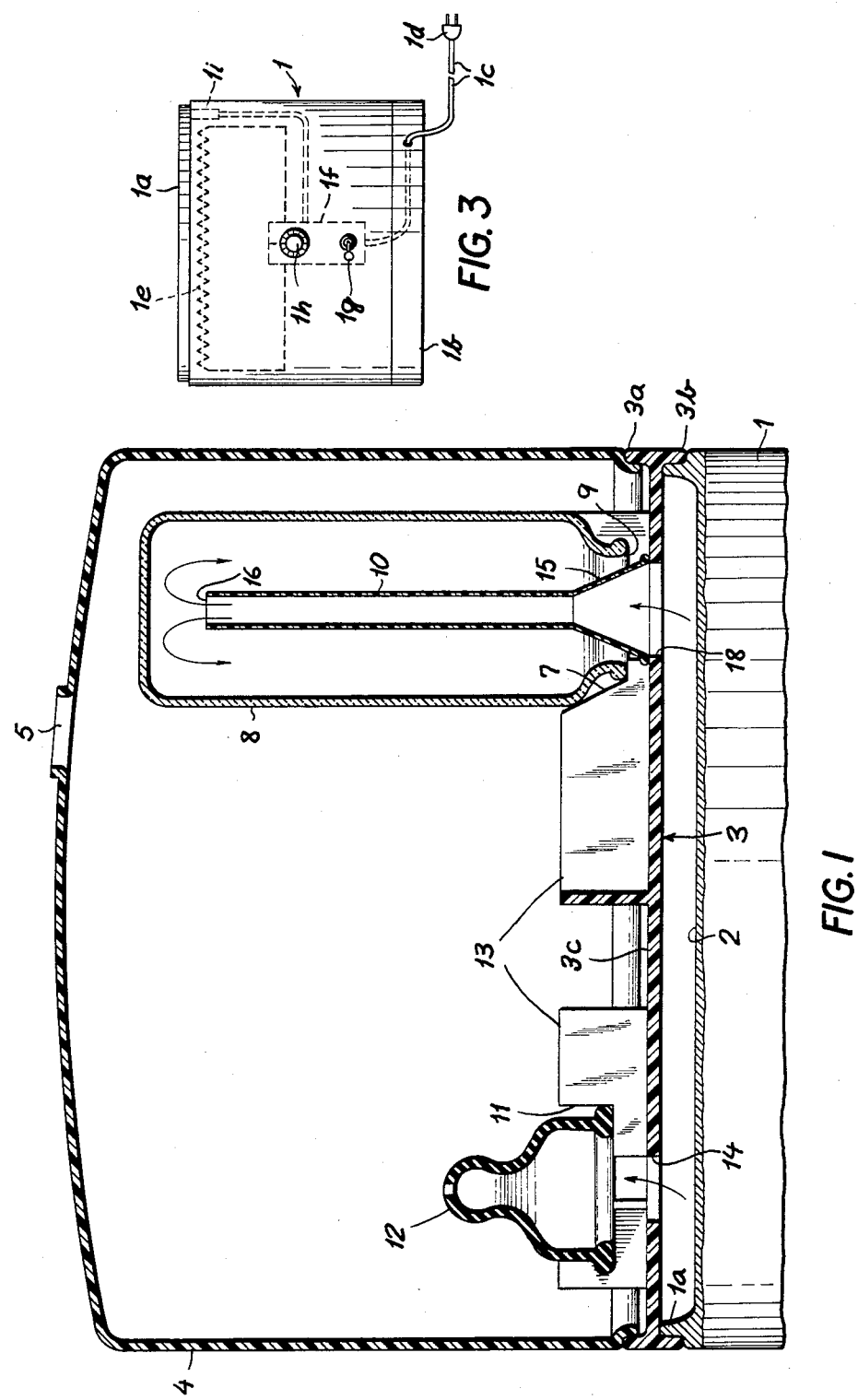
FIG. 1 is a vertical section through the upper portion of a sterilizer generally taken along the line I—I of FIG. 2.
Figure 2:
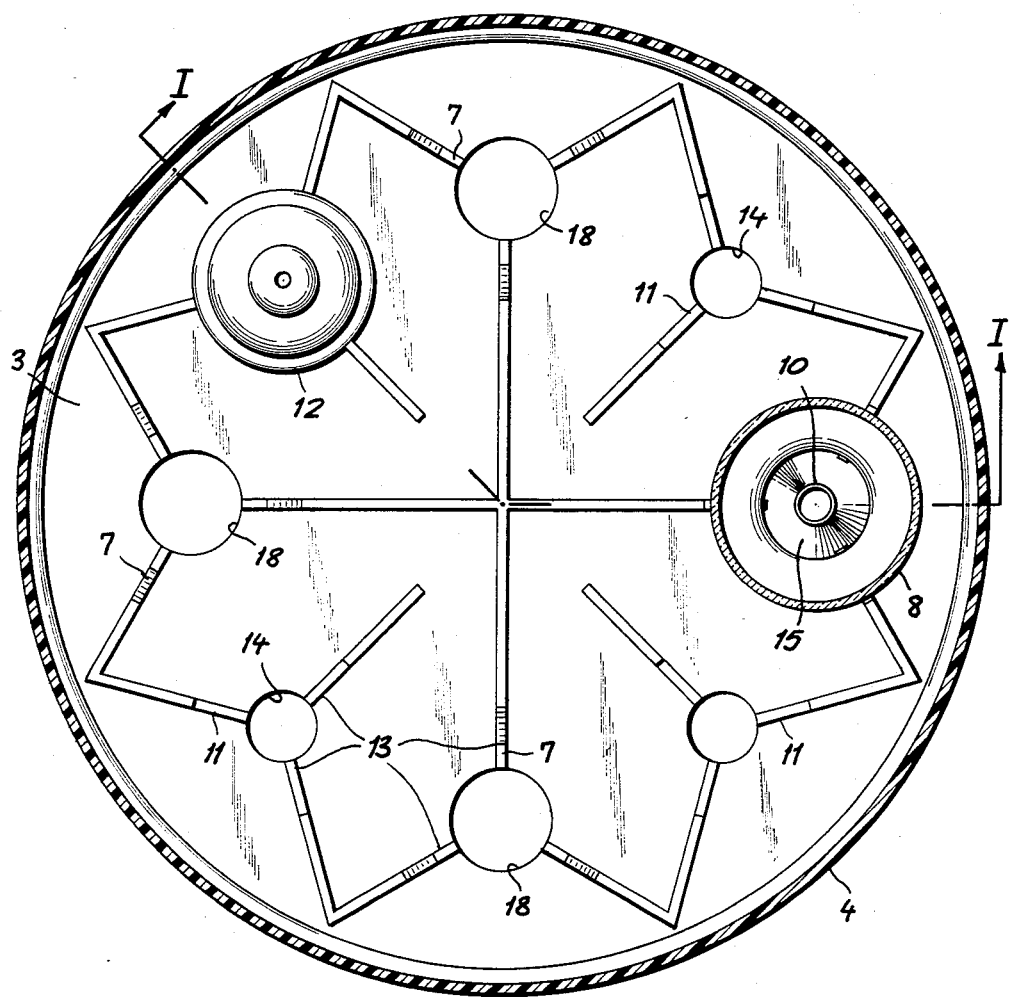
FIG. 2 is a plan view of the insert of this sterilizer.

As can be seen from FIG. 3, the base has an upstanding flange 1a surrounding the cooking pan and adapted to receive the insert 3 which is especially configured (FIGS. 1 and 2) to hold one or more bottles and one or more nipples in position for sterilization.

Below the water-receiving pan 2, there is provided a heating coil 1e. The base 1 rests upon a table or other surface and its other portion 1b through which a wire 1c is provided with a conventional plug 1d to connect the unit to a source of electric current. The apparatus is also provided with a monitoring and cut-off circuit represented generally at 1f and including an on-and-off switch 1g and a timer 1h for timing the duration of the heating operation. A thermosensor 1i is also connected to the circuit and responds to a rise in temperature of the pan 2 above 100° C. to cut off the supply of electrical current to the heating coil 1e in the event that all water boils out of the pan.

The apparatus also comprises the hood 4 which is elongated to accommodate commercially available long bottles 8 as well as shorter bottles 8 which may be used from time to time.

At its top, the hood 4 is provided with a vent opening 5 and along its bottom portion with an inwardly turned flange engageable in an outer rib 3a of the insert 3. The latter has a lower rib 3b which rests around the flange 1a previously mentioned.

The insert 3 here comprises a plurality of seats 7 for infant feeding bottles 8, only one of which has been shown in the drawing, angularly equispaced with seats 11 for nipples of which one has been shown at 12 in the drawing. These seats are formed by upstanding ribs 13 which lie at 120° offset from one another about the axis of each seat.

Each nipple seat 11 is formed with a bore 14 for delivering steam upwardly to the downwardly open nipple 12 and, between the ribs 13, around the outside of the nipples.

The steam also flows around the outsides of the bottles 8.

Within each seat 7 for the bottles 8, a frustoconical funnel 15 delivers the steam rising through an opening 18 to a tube 10 which carries the steam close to the upper end of the bottle. The mouth 16 of the tube thus terminates below the bottom of the inverted bottle. The tubes 10 and their funnels 15 may be unitary with one another and composed of a heat-resistant synthetic resin such as a polycarbonate. They may be replaceable so that the tubes can have different lengths depending upon the length of the bottles sterilized.

The ribs 13 form with the bottom plate 3c and the ribs 3a and 3b of the insert a unitary body composed of heat-resistant synthetic resin, e.g. polycarbonate.

Additional openings can be provided in the plate 3c to the extent necessary to permit condensate to return to the pan 2.

In operation, the pan 2 is filled with water, the insert 3 is applied to the upper end of the base 1, the desired number of bottles and nipples are provided on the respective seats so that the mouths 9 thereof are turned downwardly. The hood 4 is then fitted over the assembly and the device turned on.

The water boiling in the pan 2 is converted to steam which rises into the nipples and bottles and around the nipples and bottles to sterilize the latter.

The sterilization time can be set by the timer or can be terminated simply by allowing the water to boil out whereupon the sensor 1i will deenergize the heater.

I claim:

1. A bottle sterilizer attachment for an egg cooker having a base provided with an upwardly open water receiving pan, an electric heater below said pan for heating and boiling water thereon, and means for cutting off said electric heater, said attachment comprising:
    a synthetic resin plate formed unitarily with a downwardly extending ridge engageable over a rim of an upwardly open water receiving pan, an upwardly extending ridge along an outer periphery of said plate, a multiplicity of flat plate-like upstanding ribs with cut out portions oriented such that three angularly equispaced ribs at each of a multiplicity of locations so as to define recesses therein providing for a plurality of seats including bottle seats dimensioned to receive infant-feeding bottles and nipple seats dimensioned to receive nipples for said bottles, said plate being provided with respective openings within said seats for permitting steam formed in a pan to rise through said openings and contact bottles and nipples located on said seats;
    respective upwardly extending tubes aligned with the openings of said bottle seats having upwardly converging frustoconical bases covering the openings of said bottle seats whereby steam is delivered to the upper end of inverted bottles placed on said bottle seats, said bottle seats holding said bottles out of contact with said bases; and a hood of a height greater than that of said bottles removably formed over said plate and engaging said upwardly extending ridge, said hood having a vent, said ribs defining passages beneath said seats communicating with the space within said hood surrounding the bottles and nipples.

2. A sterilizer for infant-feeding articles including at least one bottle and at least one nipple, said sterilizer comprising:

a base provided with
  an upwardly open pan for receiving water,
  an electric heating element energizable for boiling water contained within said pan, and
  monitoring means for deenergizing said element;

an insert in the form of a plate receivable on said base above said pan and provided with at least one holder for such articles, said holder being formed with steam-delivery means for supplying steam formed by the boiling of water in said pan to at least one of said articles in said holder; and a hood adapted to fit over said insert and to enclose said article thereon said insert being formed with a plurality of seats each adapted to receive one such article, at least some of the seats receiving bottles and others of said seats receiving nipples, said hood having a height sufficient to permit it to enclose infant feeding bottles disposed on respective seats on said insert, each of said seats communicating with a space below said insert and above said pan via a respective opening formed in said insert, the seats receiving said bottles being provided with means for conducting steam to the upper end of each bottle when the same is positioned on one of said seats, the steam-conducting means including a tube opening close to an upper end of a bottle on one of said seats and formed with a frustoconical lower end converging upwardly and disposed inwardly of the respective seat over one of said openings, said plate including a plurality of flat, upstanding plate-like ribs with said ribs cut out so as to form recesses therein providing for said plurality of seats.

3. The sterilizer defined in claim 2 wherein said hood is provided with a vent opening at an upper end thereof.

4. The sterilizer defined in claim 3 wherein said hood is formed from synthetic resin material.

* * * * *